(12) United States Patent
Huo et al.

(10) Patent No.: US 8,588,485 B2
(45) Date of Patent: Nov. 19, 2013

(54) RENDERING FOR IMPROVED DIAGNOSTIC IMAGE CONSISTENCY

(75) Inventors: Zhimin Huo, Pittsford, NY (US); Jianqing Y. Bennett, Honeoye Falls, NY (US); David H. Foos, Rochester, NY (US); Huihai Lu, Pu Dong (CN); Jing Zhang, Huang Pu (CN)

(73) Assignee: Carestream Health, Inc., Rochester, NY (US)

( * ) Notice: Subject to any disclaimer, the term of this patent is extended or adjusted under 35 U.S.C. 154(b) by 946 days.

(21) Appl. No.: 12/482,651

(22) Filed: Jun. 11, 2009

(65) Prior Publication Data

US 2010/0128063 A1    May 27, 2010

Related U.S. Application Data

(60) Provisional application No. 61/117,640, filed on Nov. 25, 2008.

(51) Int. Cl.
*G06K 9/00*    (2006.01)

(52) U.S. Cl.
USPC ........... 382/128; 382/131; 382/132; 382/254; 382/274; 600/458

(58) Field of Classification Search
None
See application file for complete search history.

(56) References Cited

U.S. PATENT DOCUMENTS

| | | |
|---|---|---|
| 4,302,672 A | 11/1981 | Kato et al. |
| 5,268,967 A | 12/1993 | Jang et al. |
| 5,357,549 A | 10/1994 | Maack et al. |
| 5,633,511 A | 5/1997 | Lee et al. |
| 5,835,618 A | 11/1998 | Fang |
| 6,778,691 B1 | 8/2004 | Barski et al. |
| 7,221,786 B2 | 5/2007 | Luo et al. |
| 7,266,229 B2 * | 9/2007 | Couwenhoven et al. ...... 382/132 |
| 2002/0181797 A1 * | 12/2002 | Young ........................... 382/260 |
| 2003/0053673 A1 * | 3/2003 | Dewaele ....................... 382/132 |
| 2005/0018894 A1 * | 1/2005 | Couwenhoven et al. ..... 382/132 |
| 2005/0171409 A1 * | 8/2005 | Arimura et al. ............... 600/300 |
| 2006/0261296 A1 * | 11/2006 | Heath et al. ................... 250/580 |
| 2007/0269095 A1 * | 11/2007 | Couwenhoven et al. ..... 382/132 |
| 2007/0269106 A1 | 11/2007 | Huo et al. |
| 2008/0002906 A1 * | 1/2008 | Wang et al. .................... 382/270 |
| 2008/0118139 A1 | 5/2008 | Huo et al. |

* cited by examiner

*Primary Examiner* — Matthew Bella
*Assistant Examiner* — Jason Heidemann

(57) ABSTRACT

A networked system for rendering diagnostic image data for display has at least one diagnostic imaging apparatus that obtains digital image data for a patient and is in communication with a computer network. At least one consistency control module executes at a networked processor and is operatively responsive to a set of programmed instructions for accessing and detecting the type of image, for identifying one or more control points in the obtained digital image data, for mapping the input code values of the one or more control points to corresponding predetermined code values, for mapping additional input code values to output values according to the mapping of the one or more control points, and for providing rendered image data as output. A DICOM destination in networked communication with the at least one consistency control module stores or displays the rendered image data.

19 Claims, 15 Drawing Sheets

RENDERING FOR IMPROVED DIAGNOSTIC IMAGE CONSISTENCY

CROSS REFERENCE TO RELATED APPLICATIONS

Priority is claimed from U.S. Ser. No. 61/117,640 entitled "ROI-BASED RENDERING FOR DIAGNOSTIC IMAGE CONSISTENCY" by Zhimin Huo and Jianqing Y. Bennett provisionally filed on Nov. 25, 2008, published as US 2007/0269106, incorporated herein by reference.

FIELD OF THE INVENTION

This invention generally relates to processing of diagnostic images and more particularly relates to a method and system for enhancing one or more diagnostic images in order to provide consistent rendering for a region of interest (ROI) based on analysis of image content over that region.

BACKGROUND OF THE INVENTION

Consistency in image rendering helps to allow a more accurate clinical evaluation when using x-rays and related types of diagnostic images. Images taken of the same anatomy that have the same overall dynamic range and contrast settings can be more readily compared against one another for diagnosis and for tracking various conditions, particularly for images taken of the same patient at different times and on different imaging apparatus. In an Intensive Care Unit (ICU), for example, a succession of diagnostic images taken over a time period may help to show the progress of a patient's condition and help to direct ICU treatment accordingly.

In practice, however, consistent image rendering has proved difficult to achieve. Differences in image quality from one image to the next can be significant, owing to differences in exposure settings, patient and apparatus positioning, scattering, and grid application, for example. Thus, even for images obtained from the same patient over a short treatment interval, there can be substantial differences between two or more images that prevent effective comparison between them and constrain the ability of the clinician to detect subtle changes that can be highly significant. This problem relates to images whether originally obtained on film and scanned, or digitally obtained, such as using a computed radiography (CR) or digital radiography (DR) system.

Computed radiography systems that use storage phosphors and digital radiography systems can offer a very wide exposure latitude (as much as 10,000:1 compared with that available from conventional screen/film systems (typically 40:1). This means that exposure error is much less serious for computed radiography at the time of image sensing and recording. However, image display apparatus have a much more limited dynamic range. Tone scale mapping in computed radiography can be specifically tailored to provide an optimal rendition of every individual image. However, most output media, such as photographic film and displays such as flat-panel or cathode ray tube (CRT) displays do not have wide enough dynamic range to display this information at nearly 10,000:1 latitude with proper visual contrast. It is, therefore, necessary to carefully allocate the available output dynamic range to display the clinically important part of the input code values.

For some applications, the range of the region of interest in the input image may exceed that provided by the output media or display, and the contrast of parts of the input image may then be compromised as a result. For example, U.S. Pat. No. 4,302,672 entitled "Image Gradation Processing Method And Apparatus For Radiation Image Recording System" to Kato et al. teaches a method of constructing such a compromised tone-scale curve for chest x-ray images. However, that method uses the valleys and peaks of the code-value histogram to identify the critical points between the spine, the heart, and the lung. The results are not very reliable because these valleys and peaks are not always clearly detectable. This method requires that all images obtained have the same overall spatial profile, which need not be true. Furthermore, the method cannot be generalized to examinations other than chest images.

From one perspective, there are chiefly five classes of "objects" in radiographic images: (1) foreground (collimator blades used to protect parts of the body from unnecessary x-ray exposure) usually corresponding to very low to low exposure areas; (2) man-made objects (such as pacemakers, tubes, and electrodes); (3) soft tissues (such as muscles, blood vessels, and intestines) usually corresponding to low (e.g., mediastinum) to high (e.g., lung) exposures depending on tissue thickness; (4) bones corresponding to low to very low exposure levels (often overlapping with the foreground); and (5) background corresponding to very high exposure areas. These five classes of objects can be difficult to separate using the code value alone, because there can be considerable overlap between objects in different classes (such as with the bone and the collimator blades).

As has been noted in commonly assigned U.S. Pat. No. 5,633,511 entitled "Automatic Tone Scale Adjustment Using Image Activity Measures" to Lee et al., some basic problems in adjusting tone scale for computed radiography relate to: (1) determining which sub-range of the input code values is most important for clinical evaluation and (2) constructing a tone-scale transfer curve so that the important sub-range of the code values identified in step (1) can be rendered with proper contrast and brightness (density) on the output display or media. For example, the digital code values of an input chest x-ray image may span from 500 to 3000 (in units of 0.001 log exposure), but the code value range of the lung area, being the most important region of the image, may only span from about 1800 to 2600. Simply mapping the entire range of the input code value (from 500 to 3000) to the available film density range with equal contrast for all input code values can produce a chest image with an unacceptably low contrast, making it difficult to discern features clearly. It is, therefore, very useful to have an algorithm to automatically detect and select the relevant sub-range of the input code values (typically 1800 to 2600) to display on the output media with proper visual contrast and brightness. The process of selecting the relevant sub-range of input code values and constructing the proper mapping function from the input code value to the output display media is termed tone scale adjustment.

The Lee et al. '511 disclosure describes conventional approaches for identifying the sub-range of interest in the image, using a histogram of input code values, then discloses an improved alternative for identifying this sub-range, using an activity histogram. The activity histogram disclosed in the Lee et al. '511 patent gives a measure of line-by-line image activity that improves overall image rendering and has advantages for achieving improved image contrast and brightness.

Expanding upon the techniques of the Lee et al. '511 patent, a contrast enhancement method is also disclosed in commonly assigned U.S. Pat. No. 6,778,691 entitled "Method Of Automatically Determining Tone-Scale Parameters For A Digital Image" to Barski et al. The method of the Barski et al. '691 disclosure automatically generates a Look- Up Table (LUT) for obtaining a desired tone scale for an image, using the slope of the tone scale curve over its midrange densities.

Conventional methods for adjusting the intensity range and slope of diagnostic image values may not provide satisfactory results in all cases. While methods such as those described in the Lee et al. '511 patent and in the Barski et al. '691 patent provide improvements in contrast enhancement for a diagnostic image, these methods do not address the problem of consistent rendering between images taken for a patient at different times or for images of different patients. Thus, for example, where two or more images for a patient taken at different times differ with respect to exposure values or other values, application of such contrast improvement techniques is not likely to provide consistent rendering that would allow more accurate assessment of condition changes by the ICU clinician.

Contrast stretching is one method that has been proposed for providing a measure of normalization between images. For example, U.S. Pat. No. 5,357,549 entitled "Method Of Dynamic Range Compression Of An X-Ray Image And Apparatus Effectuating The Method" to Maack et al. describes a dynamic range compression technique that stretches image intensity in only a particular area of interest, such as within the lung area of a chest X-ray. The proposed method locates low frequency components, determines equalization factors, and then applies these to the image for compressing low frequency components, freeing the remainder of the dynamic range for higher frequency areas of the image intensities. In a similar approach, U.S. Pat. No. 5,835,618 entitled "Uniform And Non-Uniform Dynamic Range Remapping For Optimum Image Display" to Fang uses a method of dynamic range remapping for enhancing the image in both dark and bright intensity areas. This remapping or correction technique amounts to smoothing the data (such as through a low-pass filter), determining the data mean, adjusting the smoothed data to the mean, and then applying smoothed, adjusted data to the original data. Methods such as those described above focus on improving the overall image appearance of individual images, which may in turn help to improve image consistency to some degree. However, these and other conventional contrast-stretching methods do not directly address inconsistency from image to image.

Thus, in spite of continuing attempts to achieve acceptable diagnostic quality of individual images, there remains considerable room for improvement in achieving an acceptable measure of consistency in diagnostic image rendering. The problem of providing consistency in image appearance is complicated by the number of different types of imaging systems that can be used, each having different preprocessing of the initial image data, by imaging techniques applied during the exam, and by viewer preferences for image content from different regions of interest. It would be beneficial to provide solutions to the rendering problem that provide consistent results for the same types of images taken over a period of time, such as for patients in an ICU or similar care facility.

SUMMARY OF THE INVENTION

It is an object of the present invention to advance the art of diagnostic imaging with respect to image consistency. With this object in mind, the present invention provides a networked system for rendering diagnostic image data for display, the system comprising: at least one diagnostic imaging apparatus that obtains digital image data for a patient and that is in communication with a computer network; at least one consistency control module that executes at a networked processor on the computer network and that is operatively responsive to a set of programmed instructions that comprise: instructions for accessing the obtained digital image data and for detecting the type of image for the digital image data obtained from the networked diagnostic imaging apparatus; instructions for identifying one or more control points in the obtained digital image data; instructions for mapping the input code values of the one or more control points to corresponding predetermined code values; instructions for mapping additional input code values to output values according to the mapping of the one or more control points; instructions for providing rendered image data as output according to the mapped output values; and a DICOM destination in networked communication with the at least one consistency control module for storing or displaying the rendered image data.

It is a feature of the present invention that it provides a method for improving the rendering consistency of radiographic images based on characteristics of the regions of interest (ROIs) or features of the image.

It is a feature of the present invention that it addresses image consistency in the output space by allocation of gray scale range and by assigning boundary values for a given ROI.

It is an advantage of the present invention that it adapts to different imaging apparatus and equipment, so that images taken at different times or on different imaging systems can be processed and compared against each other.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings.

DETAILED DESCRIPTION OF THE INVENTION

Figure 1A:
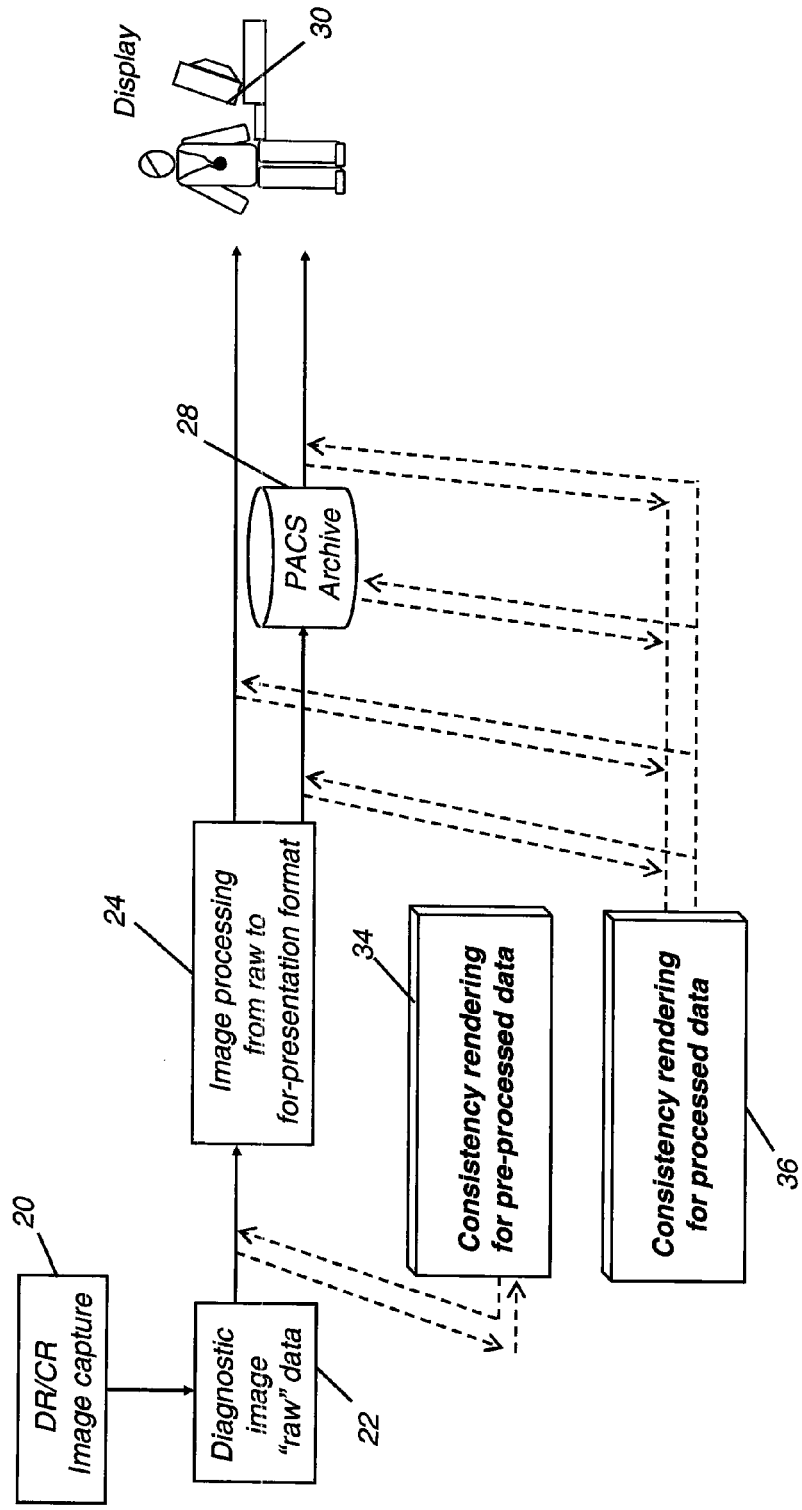
FIG. 1A is a block diagram of image data flow within a medical imaging system in which the method of the present invention can be used.

The present description is directed in particular to elements forming part of, or cooperating more directly with, apparatus in accordance with the invention. It is to be understood that elements not specifically shown or described may take various forms well known to those skilled in the art.

Reference is made to U.S. Patent Application Publication No. 2008/0118139 entitled "ROI-based Rendering for Diagnostic Image Consistency" by Huo et al. filed 22 Dec. 2006, commonly assigned, and incorporated herein by reference.

The term "DICOM destination" refers to a device on a DICOM (Digital Imaging and Communications in Medicine) network. By definition, a DICOM destination could be a display or an archival system, such as a PACS (Picture Archiving and Communications System) that uses one or more computers or networks dedicated to the storage, retrieval, distribution, and presentation of medical images. The most common standard format for image storage is DICOM format.

The present invention provides ROI-based gray-scale normalization for consistent rendering of diagnostic images. The method of the present invention provides a remapping of density values for diagnostic images that provides a consistent rendering of images that may have been taken at different times and under different conditions, including images obtained from different imaging systems. Consistent rendering of images allows the clinician to more easily compare images of the same patient or of the same anatomy and can help to provide more efficient and accurate diagnosis.

The processing of the present invention is performed, at least in part, on a computer or other type of control logic processor, such as a dedicated image processor, for example. In the context of the present disclosure, the term "networked processor" is used to identify the computer or other type of processor that executes programmed instructions for consistency control. The computer or other type of control logic processor that is used as the networked processor is equipped with and in communication with the needed electronic data storage and memory circuitry for executing programmed logic instructions and for storing results. The computer may include one or more storage media, for example; magnetic storage media such as magnetic disk or magnetic tape; optical storage media such as optical disk, optical tape, or machine readable bar code; solid-state electronic data storage devices such as random access memory (RAM) or read-only memory (ROM); or any other physical device or media employed to store a computer program having instructions for controlling one or more computers and related data to practice the method according to the present invention.

To illustrate the methods of the present invention, the description in this section is directed to chest x-rays in one exemplary embodiment. However, the method of the present invention is not limited to any one type of radiological image, but can be used for imaging other parts of the body as well.

Unlike earlier consistent rendering methods, embodiments of the present invention can operate on a single image, not requiring the use of multiple images for obtaining suitable image rendering parameters. In addition, the consistent rendering methods of embodiments of the present invention are advantaged over earlier consistent rendering approaches since they are not limited to one type of data or imaging system but can be applied either to pre-processed or "raw" image data directly as obtained from a DR or CR system or film scanner, or to processed data that has been readied for display or printing. Referring to FIG. 1A, there is shown a block diagram of the imaging chain for captured diagnostic images, with the possible points of access to consistent rendering software provided in embodiments of the present invention. The programmed software modules for data processing to provide consistency control shown and described with reference to FIG. 1A execute on one or more networked computers or other logic processors, according to programmed instructions.

Figure 1B:
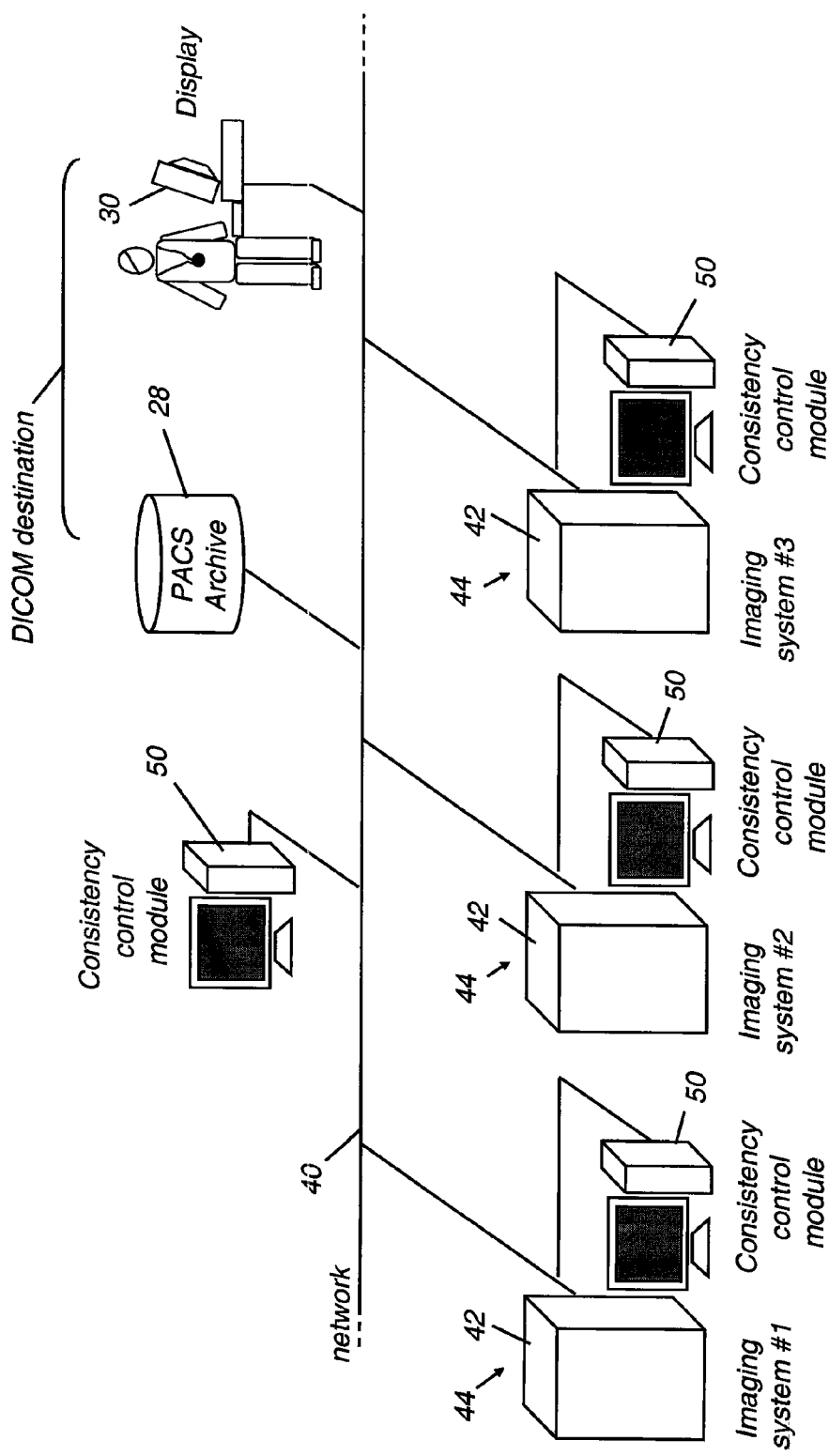
FIG. 1B is a block diagram showing a network with a number of consistency control modules at different networked locations in one embodiment of the present invention.

Tracing the basic image processing chain in FIG. 1A, an image capture device 20 obtains unprocessed or "raw" image data 22 that is processed by an image processing system 24 and is provided directly to a networked DICOM destination, which could be either a display 30, as shown in FIGS. 1A and 1B, or a PACS archival system 28, for example. A consistent rendering processor 34 can optionally be provided for providing consistent rendering to the pre-processed data. Alternately, an optional consistent rendering processor 36 can be provided for handling processed data that may have already been rendered. As represented in FIG. 1A, this processing can include image data accessed at any of a number of points along the imaging chain, including prior to or following PACS archival. The consistency rendering of the present invention can be used in any of a number of embodiments, including with any of a number of types of different image capture devices 20.

In the block diagram of FIG. 1B, a network 40 connects with a number of imaging sites, 44 and with PACS archival system 28. Each imaging site 44 shown in the embodiment of FIG. 1B has a corresponding consistency control module 50 for images obtained at an imaging system 42. Consistency control module 50 may also be independent of any specific imaging system 42 and located at any accessible networked location, so that it is effectively in communication with more than one imaging system 42. Consistency control module 50 can execute within a specific host computer or other control logic processor or may be a network program that executes on a remotely located, networked server. As a hardware or software component, consistency control module 50 receives and executes entered and stored programmed instructions to detect the type of diagnostic image, to identify information such as imaging source, detectors, and their manufacturers, and to identify body parts examined and one or more regions of interest (ROIs) from within the image, to obtain and determine the necessary control parameter values for the detected type of image and ROIs, to process the image using the control parameters for remapping image data, and to provide the processed, rendered image as output.

Network 40 can be any suitable network type, including an Ethernet network, for example. This may be a proprietary local area network (LAN) located within a hospital or other facility or may be an internet-accessible network with appropriate security safeguards for privacy of patient data.

With the modular control logic arrangement shown in FIG. 1B, consistency can be obtained according to a standard that is stored on the network and used by each consistency control module 50. Alternately, a number of consistency variables or parameters can be stored and used, including consistency parameters specific to each imaging system 42. This enables consistency between systems, so that the image obtained and displayed from imaging system #1 can have consistent appearance with an image obtained and displayed from imaging system #3, for example. Similarly, two images taken at different times can be provided with consistent rendering in order to facilitate their comparison.

Figure 1C:
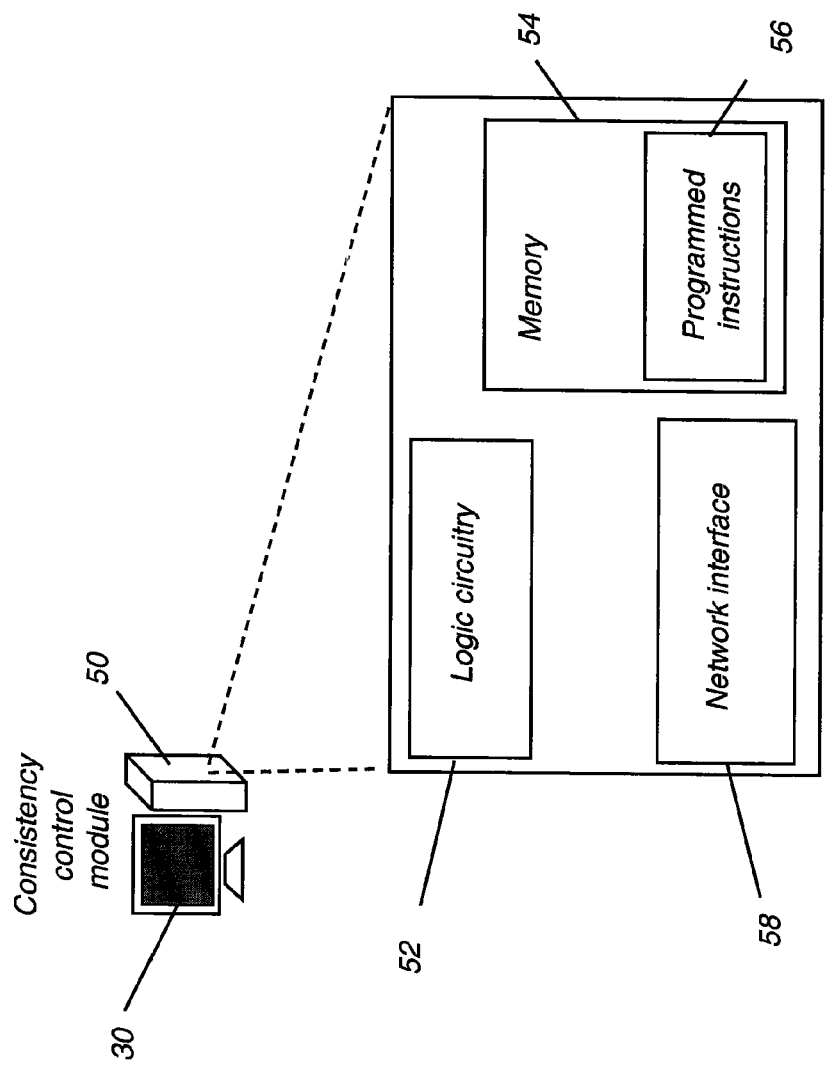
FIG. 1C is a schematic block diagram that shows components that execute functions of consistency control on a computer or other processor.

The schematic block diagram of FIG. 1C shows control logic components that execute functions of consistency control module 50 on a computer or other processor. Logic circuitry 52 provides the control logic that operatively responds to and executes instructions 56 that are stored in a memory 54. A network interface 58 then enables communication of unprocessed and processed image data over the network. The stored instructions are a set of programmed instructions that can include instructions for obtaining an image from a networked apparatus; instructions for detecting the type of image obtained from the networked imaging apparatus; instructions for determining and obtaining variable control parameters and values; instructions for identifying one or more control points in the obtained digital image data; instructions for mapping the input code values of the one or more control points to corresponding predetermined code values; instructions for mapping additional input code values to output values according to the one or more control points; instructions for rendering the diagnostic images; and instructions for providing rendered image data as output. Rendered images are then directed to a DICOM destination, such as display 30 that may be located at any suitable point in the network for viewing by the diagnostician. An alternate DICOM destination would be a PACS or other type of archival system.

Figure 2:
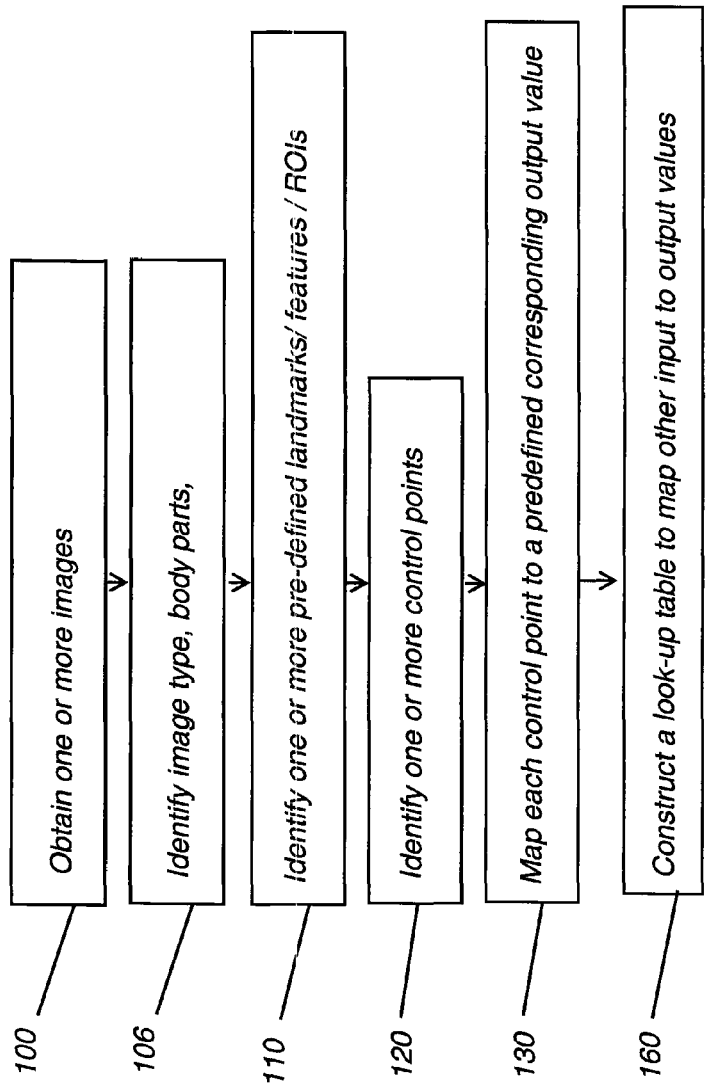
FIG. 2 is a logic flow diagram showing consistent rendering processing according to one embodiment of the present invention.

The logic flow diagram of FIG. 2 shows processing that is executed for consistent rendering by consistency control module 50 in one embodiment. More detailed description, given subsequently, then expands on the functions and operations executed within each step. In an initial step 100, one or more images are input to consistency control module 50 (FIG. 1C). A type identification step 106 then provides information on the type of image that has been obtained, including information on body part imaged and, optionally, information on the imaging modality or type of equipment that was used. A landmark identification step 110 follows, in which ROIs, anatomical features, and other features in the one or more images are located, allowing spatial correlation where there may be multiple images. Landmark identification step 110 includes a background/foreground segmentation utility for handling images having different amounts of background content (or having no background content).

Continuing with the description of FIG. 2, a control point identification step 120 then identifies one or more control points that are used for the re-mapping process from input values to output values that follows. Where there is only a single ROI or image feature of interest, these control points are from that ROI or feature and may indicate values of significant anatomy features or boundary points for an intensity range, as described in more detail in subsequent examples. Where there are multiple features of interest or ROIs in the image, a single control point from each ROI may be suitable, depending on the type of processing that follows. The control point or points could simply be determined using a histogram of image values, for example. Variable control parameters that determine the desired output values for mapping digital image data can be obtained in a number of ways, including the use of template images, of learned values from testing of diagnostician preferences over time, and of arbitrarily assigned values, such as values preferred by a particular diagnostician, for example. Mapping is monotonic and may use predetermined code values, that is, pre-selected or pre-calculated code values, to define output boundaries.

Continuing further with the sequence in FIG. 2, a mapping step 130 then maps at least each control point from step 120 to a predetermined gray scale value. As part of this step, an adjustment can be made for each mapping, depending on image capture variables or other parameters, such as adjustment for variation in patient or body part positioning, for variation in image exposure, and for variation with different types of pre-processing by different manufacturers, for example. Image-specific adjustments can be made to the remapping values based on analysis of the obtained image data and can depend on image content or on maximum and minimum or other relative pixel data values, on dynamic range, on mean or median value or on other computed statistical value, on aspects of the imaging technique or imaging equipment used to obtain the image, on patient condition, on demographics, on medical history, or on patient positioning. For example, an adjustment can be computed based on the average brightness of pixels within a portion of the ROI. Alternately, image-specific adjustments can be empirical, based on the experience of the viewing practitioners or those who administer the imaging system. Image-specific adjustments can be made depending on the type of anatomy or other feature that is of particular interest. In still other embodiments, image-specific adjustments can be made by comparing the obtained image data with an electronically stored template image that has been selected beforehand. For example, this may include toe-shoulder contrast adjustment that adjusts image content for very dark and very light regions.

Following any needed adjustment in mapping step 130, an LUT generation step 160 is executed. In LUT generation step 160, Look-Up Tables (LUTs) are generated for each of the one or more images submitted in initial step 100, providing consistent rendering by a remapping of the initially processed image data values.

It should be noted that methods and algorithms for identifying regions of interest in a diagnostic image are known to those skilled in the diagnostic imaging arts, as well as various techniques for mapping digital data in an input range within a region of interest to an output range.

Background Segmentation

Background segmentation, executed as part of step 110 as shown in FIG. 2, enables the image tissue content to be identified and separated from background content, so that both types of image content can be handled separately. There are a number of approaches to background segmentation, well known to those skilled in the imaging arts. The overall goal of background segmentation is to define the tissue portion of the image, isolated from non-tissue background areas. Among well known approaches are histogram analysis and manipulation, for example. For chest x-rays, as well as for other types of radiological images, background segmentation must distinguish between various image characteristics. Some images, for example, may not have background content; in other images, the amount of background content may be significant.

Identification of Landmark Features and ROIs

It should be noted that there can be multiple ROIs within the obtained image. For clarity of description, the discussion that follows shows use of a single ROI per image. Landmark identification step 110 in the logic flow diagram of FIG. 2 uses one of a number of possible methods to identify common features in a given type of image. In one embodiment, for example, the method used is similar to that disclosed in commonly assigned U.S. Pat. No. 7,221,786 entitled "Method For Automatic Construction Of 2D Statistical Shape Model For The Lung Regions" to Luo et al. Briefly, this method applies thresholding, templates, and edge gradient analysis to detect the boundaries in an image, such as lung boundaries, for example.

Figure 3:
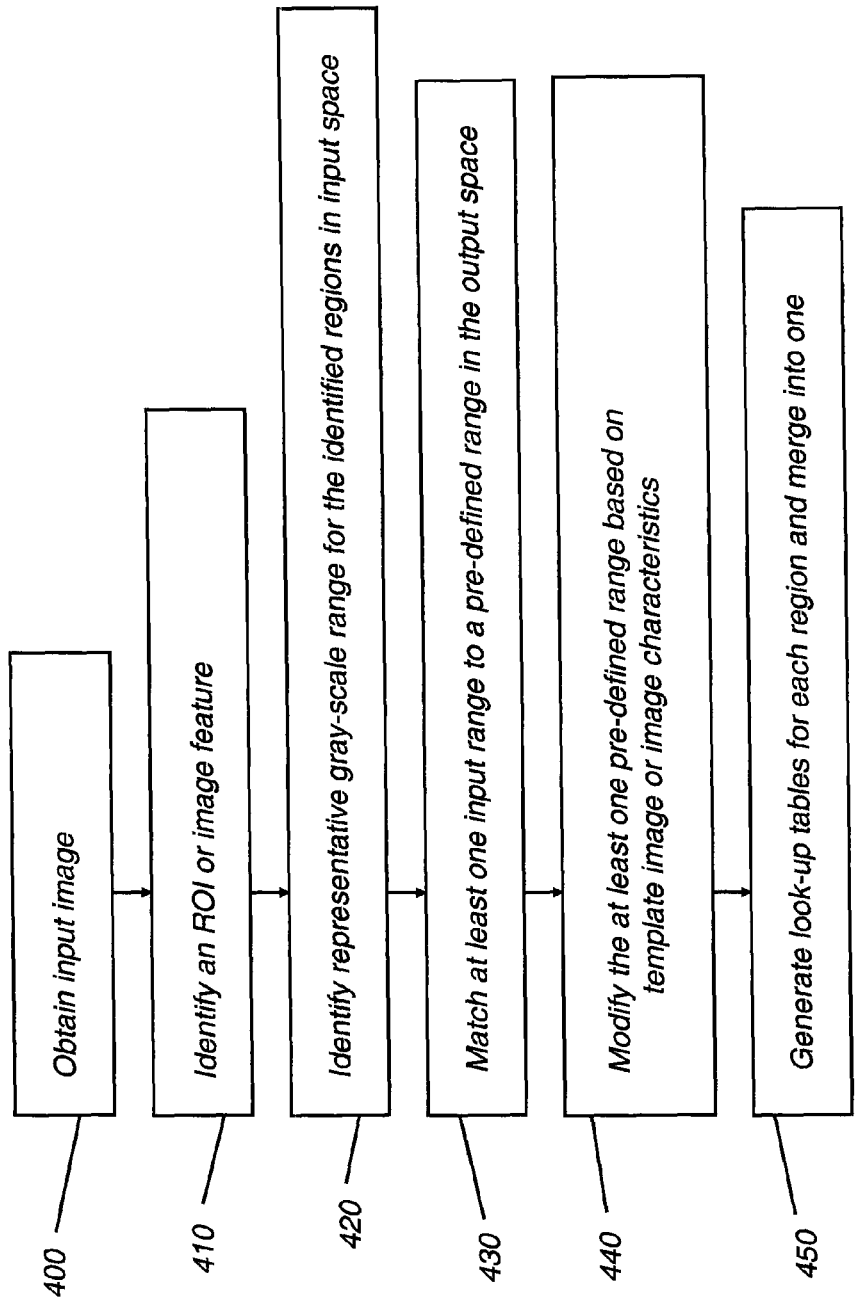
FIG. 3 is a logic flow diagram outlining the basic steps used for ROI identification and consistent rendering in one embodiment.
Figure 4:
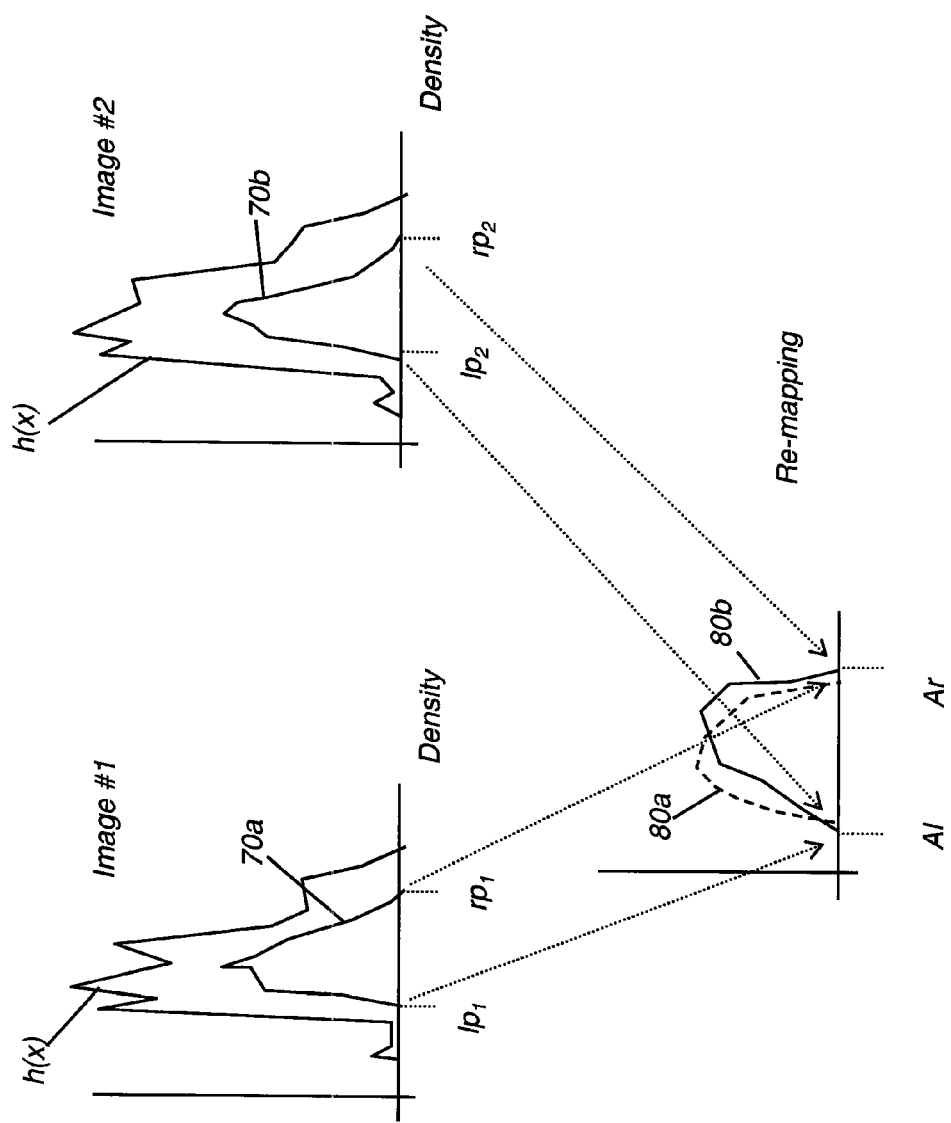
FIG. 4 shows an example of the remapping operation performed by the present invention in one embodiment.
Figure 5:
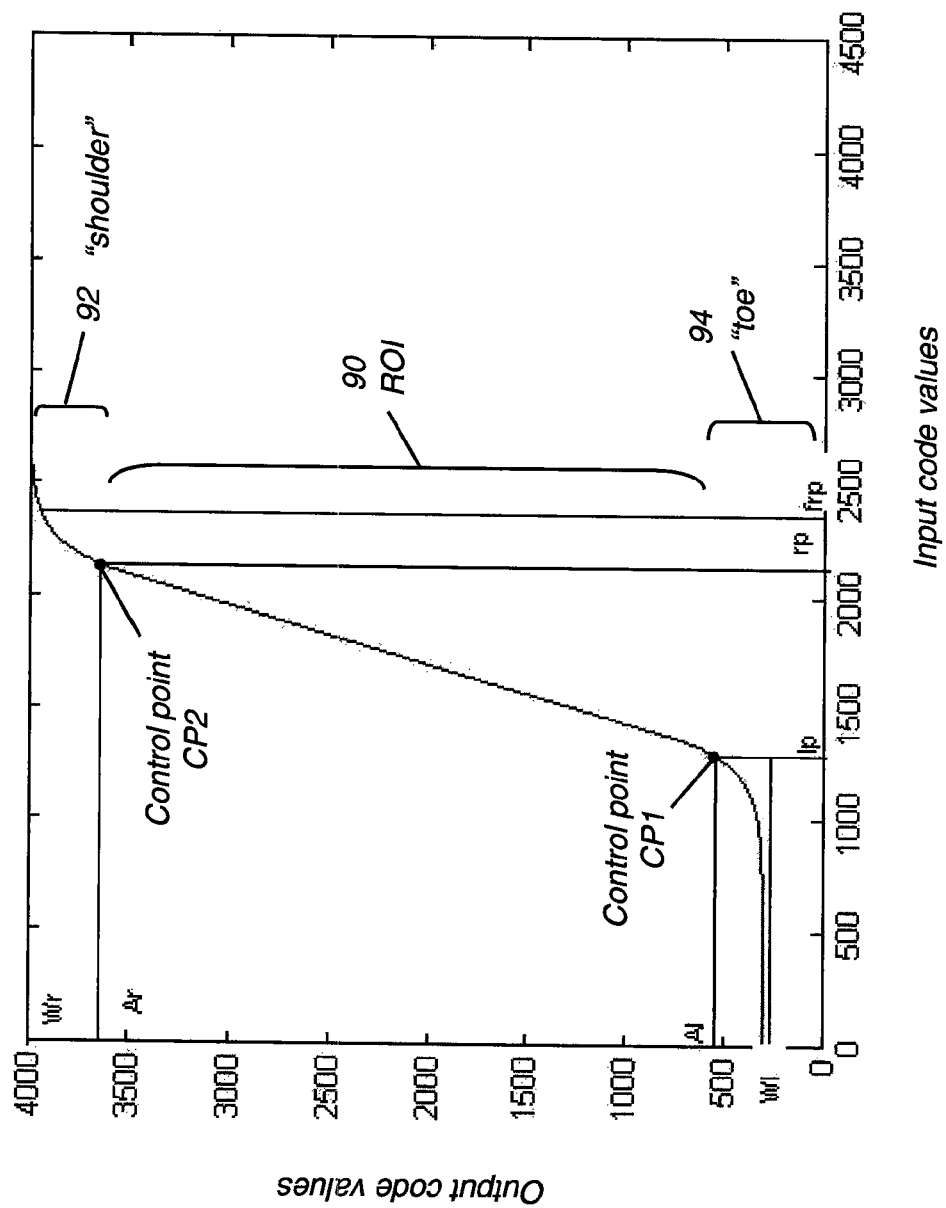
FIG. 5 is a graph showing input to output mapping for an image using the method of the present invention.
Figure 6:
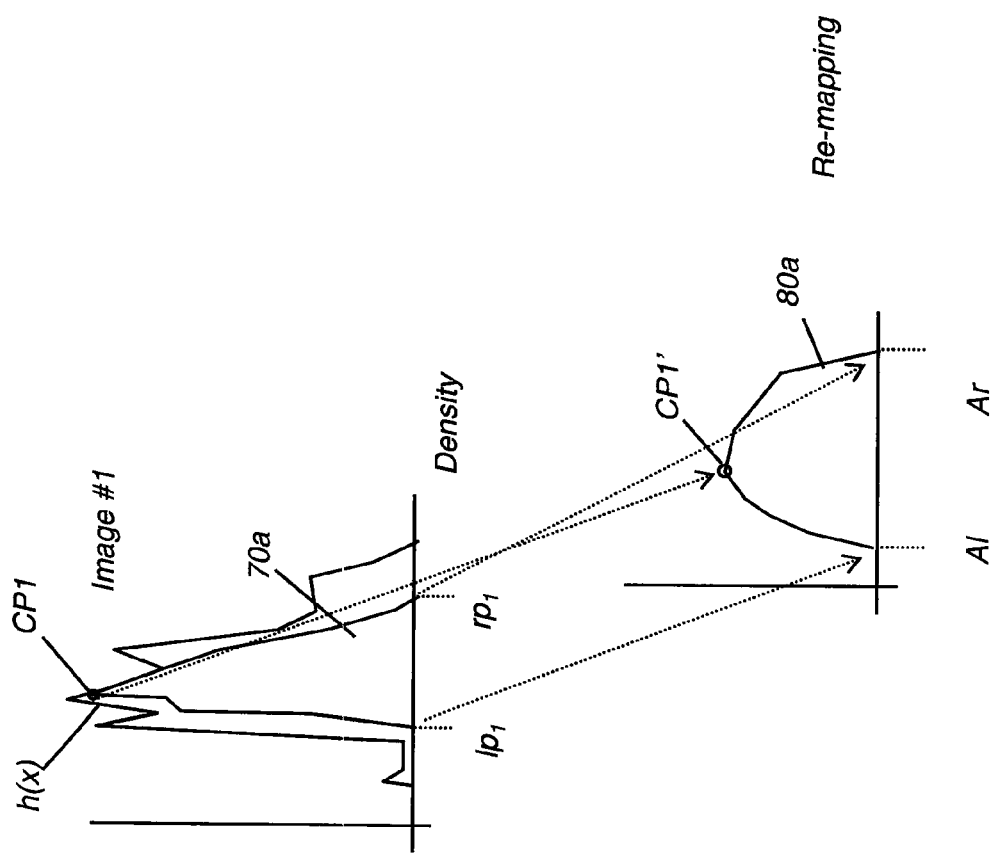
FIG. 6 shows an example of the remapping operation performed by the present invention in an alternate embodiment.

The logic flow diagram of FIG. 3 and diagrams and graphs of FIGS. 4-6 that follow give an example for executing the overall process outlined in FIG. 2 in a particular embodiment with separate ROIs from two different images. An input image 400 consists of obtained image data having one or more ROIs. An ROI identification step 410 identifies one or more ROIs or different types of anatomy in the image. A range identification step 420 identifies the target output gray-scale range for each of the ROIs identified in step 410. The output gray-scale range is defined between two boundary point values in output space. A matching step 430 then relates the individual ranges from step 420 with ROIs from step 410. A modification step 440 optionally adjusts one or more of the ranges based on the image specific contents, as described earlier. An LUT generation step 450 then generates partial look-up tables for each region and merges the individual LUT segments into a single LUT for rendering the image.

Identifying Control Points (CPs) and Their Adjustments (Delta $\Delta$)

Control points (CPs) for consistency mapping can be selected for their relative significance based on factors such as: (i) empirical experience, (ii) clinical relevance, or (iii) viewer preference. Empirical experience, for example, may indicate that a specific value works best for rendering of clear lung areas or for other specific types of tissue. Clinical relevance bases CP determination on factors such as the relative relevance of particular tissue to the diagnostic requirement. Viewer preference can be based on factors such as contrast settings or overall lightness or darkness, for example, by selecting proper control points and their values. Once the control points and their values are determined, they can apply to all the images of same type in order to provide the needed consistency.

Identifying Adjustments to Control Point (CP) Settings

Control points can be fixed points. They can be also adjusted slightly to allow a measure of variability according to any of a number of factors. Adjustment to control point selection can be made based on factors such as patient positioning differences, exposure settings, equipment type or manufacturer, and pre-processing software variables, for example. In the logic flow diagram of FIG. 3, the remapping of image pixel values within the region of interest is carried out by consistency control module 50 (FIG. 1C) as a result of steps 420, 430, 440, and 450.

Continuing with this example, FIG. 4 shows, in histogram format, a re-mapping scheme that is used for image data for one or more images, according to one embodiment of the present invention. For each of images #1 and #2, a common primary area 70a, 70b is identified, using the procedures for background segmentation and ROI identification just described. Left points lp1, lp2 and right points rp1, rp2, respectively, are the control points (CPs) obtained for the images following ROI identification. The goal of these next few steps is then to remap the control points; left points lp1, lp2 and right points rp1, rp2 map to corresponding points Al and Ar to form consistent images. The lp1 and lp2 control points could be the leftmost points of areas 70a and 70b or the points beyond which lie no more than about 5% of the total area under curves for areas 70a and 70b on the left side, respectively. The rp1 and rp2 control points could be the rightmost points of areas 70a and 70b or the points beyond which lie no more than about 5% of the total area under curves for areas 70a and 70b on the right side, respectively.

FIG. 4 illustrates a common behavior for consistency re-mapping as is seen in embodiments of the present invention. As part of the transformation between left control points lp1, lp2 and right control points rp1, rp2 and their corresponding bounding values for re-mapping, Al and Ar, the range of the input data values is usually increased or "stretched". The range can be also decreased or "compressed". Primaries 80a and 80b indicate this transformed area, occupying a wider range in the histogram. It is instructive to note that primaries 80a and 80b are similar, but typically exhibit slight differences, related to slight differences in image content and conditions. It is also instructive to note that FIG. 4 simplifies the re-mapping scheme slightly, since the Al and Ar boundary values may vary slightly between the two images, as described in more detail subsequently.

For an input region (lp, rp) of the same ROI or anatomy, there can be a common output range (whose location is bounded or defined by (Al, Ar)) that is fixed for all exams of the same type (for example, for all chest x-rays), in one embodiment. The values Al and Ar can be further modified, using a difference value, as (Al+$\Delta$l, Ar+Ar), based on any of a number of variables, including imaging system-specific or image-specific adjustment variables as was described earlier.

The graph of FIG. 5 shows how the various portions of the image are remapped for consistent rendering and the relative position of values Ar and Al in the remapping of control points CP1 and CP2. Value Ar can be calculated in a number of ways. In one straightforward embodiment, right control point rp obtained from the ROI can be mapped to a value Ar that has been determined to be a practical value for a set of images of the same type. However, this approach may not adequately compensate for some differences between two images, particularly as relates to the relative location of the center of the image. As shown in FIG. 5, mapping of code values is monotonic, with output code values consistently increasing (or decreasing) with increased input code values. Monotonic mapping applies for the re-mapped control points as well as for other values that are re-mapped according to the control points.

The diagram of FIG. 6 shows, again in histogram representation, a remapping of image data values in an alternate embodiment that uses lp1 and rp1 values as control points as well as an additional control point CP1. In this example, control point CP1 is a specific value near a peak value for the ROI in image #1. This value can represent a certain type of tissue or structure within the image, for example. In this example, control point CP1 is mapped to the value CP1' in the re-mapping procedure. In this way, one or more points having specific values of interest can be re-mapped in order to have more control on the consistency of images over a particular region of interest.

In alternate embodiments, image data mapping can be performed to provide consistency in how the range of values or one or more portions of the range can be rendered. Referring back to FIGS. 4 and 6, for example, one or both of the Al and Ar values for an ROI can be adjusted prior to mapping. With respect to FIG. 5, the curve representing the remapping can have a different slope or may vary from the linear arrangement shown between lp and rp values.

Because of its diagnostic relevance, particularly with lung imaging, the lower remapping boundary value Al can be more difficult to calculate than the upper remapping boundary value Ar. In a typical calculation, the values of lp and rp are pre-determined for percentages of image data values, where these are the lower and upper boundaries of the main gray-level range of the image ROI. These values are typically within the range 2%-95% for gray level values in the ROI, for example.

Figure 7:
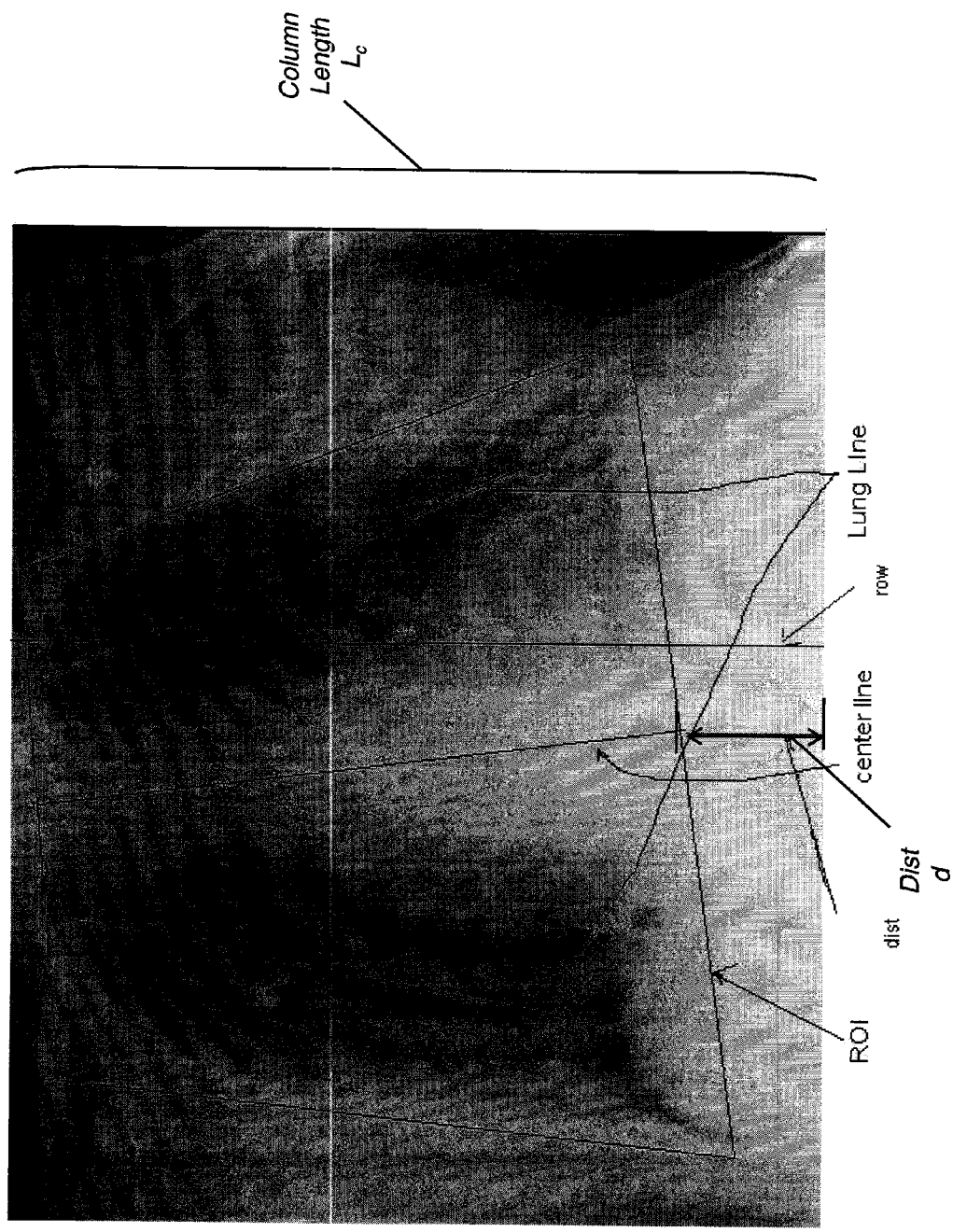
FIG. 7 shows dimensional values that can be used to help provide consistency according to image centering in one embodiment.

The example chest x-ray image of FIG. 7 shows a number of values within the image that may affect how the control points are specified in an individual case. For this example, adjustment may be made according to patient positioning. A distance d is calculated from the lower midpoint of ROIs for left and right lungs to the bottom of the image. The relative proportion of distance d to the column length $L_c$ for each image can be one factor used to the adjustment on the Ar that apply to that image. Where distance d is proportionately greater in an image, more of the abdomen and musculature appears, with corresponding effects on the image data, as can be determined from histogram or other analysis techniques.

Constructing the LUT

Figure 8:
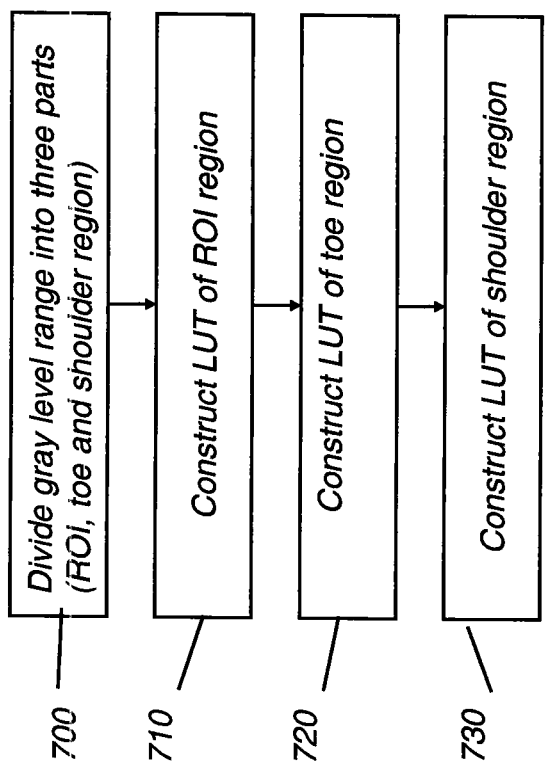
FIG. 8 is a logic flow diagram showing steps for generating a look-up table for the region of interest.

Once the Ar and Al and other control point values for mapping have been derived for an image, the LUT for its rendering can be generated. The logic flow diagram of FIG. 8 shows the overall steps used for this procedure in one embodiment. A gray level partitioning step 700 divides the gray scale range into the three parts shown in FIG. 5: a toe region 94, an ROI region 90, and a shoulder region 92. The subsequent procedures then generate LUT values for each of the three regions. An ROI region LUT construction step 710 is most significant for diagnostic imaging and is described subsequently in more detail. A toe region LUT construction step 720 then calculates the LUT values for darker, more fully exposed areas. Finally, a shoulder region LUT construction step 730 is executed for calculating values used in highlight regions.

Figure 9:
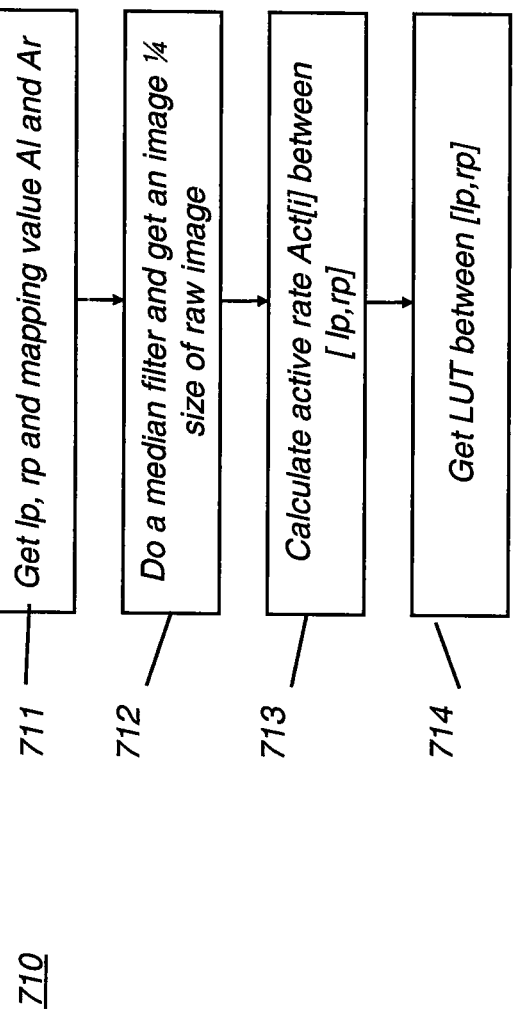
FIG. 9 is a logic flow diagram showing a sequence for LUT generation between lower and upper bounds.

The logic flow diagram of FIG. 9 shows sub-steps that are executed as part of ROI region LUT construction step 710. An obtain values step 711 is first executed to obtain values of lp and rp from the original image and lower remapping value Al and upper remapping value Ar calculated for this image. Next, an image size reduction step 712 is executed. In this step, a median filter is applied to obtain a reduced size image, ¼ the size of the original image in one embodiment. This helps to speed calculation for the steps that follow.

An image activity determination step 713 is then executed, in which image activity within the ROI is evaluated. Areas of high image activity are often clinically more significant than other areas of the image. Thus, identifying such areas helps to provide suitable imaging treatment and to enable areas of higher activity to be adjusted so that detailed information is heightened, rather than lost. This procedure may use methods disclosed in the Lee et al. '511 patent cited earlier, for example.

LUT Mapping for Regions between the Control Points

In addition to remapping the ROI region of the image, shown as a region 90 in FIG. 5, the method of the present invention is also directed to mapping darker and lighter regions. Toe-shoulder contrast adjustment procedures in step 130 (FIG. 2) perform the additional mapping that is needed for dark regions, represented as a toe region 94 in the transformation curve in FIG. 5, and for light regions, represented as a shoulder region 92 in the transformation curve in FIG. 5. Using the nomenclature shown here, points that lie to the left of lp are re-mapped to the toe region between a lower value Wl and Al. Values darker than this region are not used. Similarly, points that lie to the right of rp are re-mapped to the region between an upper value Wr and Ar. Values brighter than this region are not used.

Figure 10:
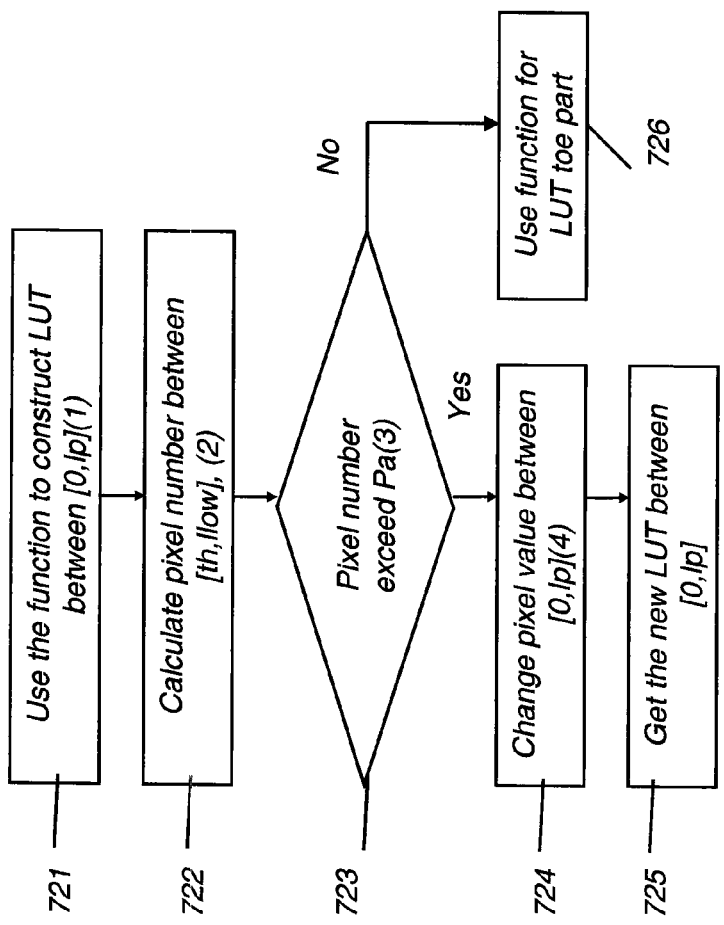
FIG. 10 shows logic flow steps for computing LUT values for the toe portion of the image data.

The logic flow diagram of FIG. 10 shows a sequence of steps for computing LUT values for the toe portion of the image data. A partial LUT construction step 721 employs a function for mapping LUT values in the region [0,lp].

The next set of steps can change the input condition of certain pixel values prior to LUT submission. A calculate pixel number step 722 follows, in which a count is obtained of the number of pixels (Pa) between a threshold value for the background th and value llow, where llow is less than lp. In a pixel number check step 723, number Pa is checked against an empirically determined threshold value to determine if a significant number of pixels have values in this region. This can indicate pixels having diagnostically relevant values. If not, a toe LUT construction step 726 is executed, remapping all toe region values for pixels i in [0, lp].

If the number of pixels having this value exceeds Pa, then a pixel value change step 724 is executed, changing the values to which LUT(i) is to be applied using:
G(i)=(lp−i)*k+i*(1−k) where 0<k<1 is a parameter that can be empirically defined. A low value LUT step 725 follows, applying LUT(i) to the remapped values.

Figure 11:
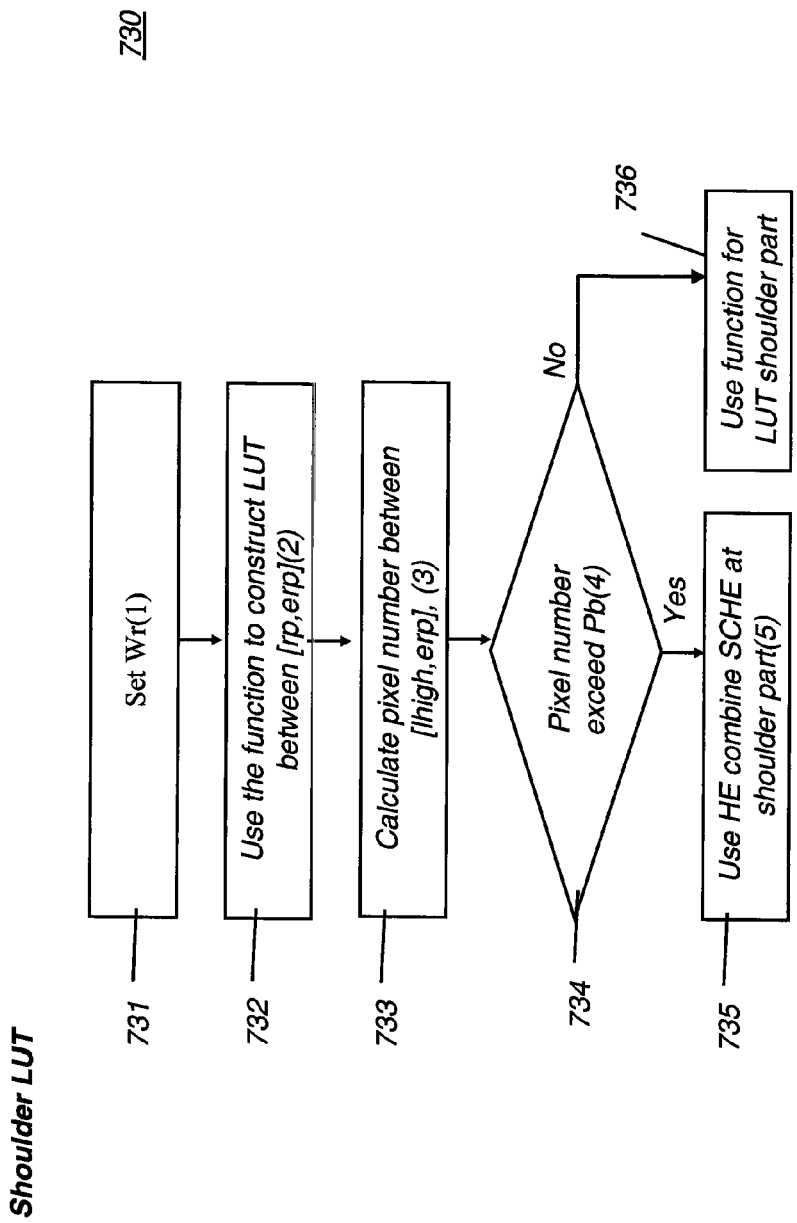
FIG. 11 shows logic flow steps for computing LUT values for the shoulder portion of the image data.

The block diagram of FIG. 11 shows logic flow steps for computing LUT values for the shoulder portion of the image data in one embodiment. In a set Wr value step 731, a value is set for upper value Wr for this patient. The erp value will be mapped to this value. Empirically determined, a typical Wr value is 3750. A partial LUT construction step 732 follows. A calculate pixel number step 733 executes next. Here, value lhigh is the gray level mapping to Wr−100 (or Wr less some other offset value) in the previous function for LUT shoulder part construction. In a pixel number check step 734, the number of values is checked against an empirically determined number Pb. If below this number, the LUT can be computed in a shoulder LUT construction step 736. This can be done, for example, using the following function:

$$LUT(i) = \left(\frac{\sum_{k=rp}^{i} h(k)}{\sum_{k=rp}^{erp} h(k)}\right) \cdot (Wr - Ar) \cdot \text{ratio} + \left(\frac{\sum_{k=rp}^{i} sh(k)}{\sum_{k=rp}^{erp} sh(k)}\right) \cdot (Wr - Ar) \cdot (1 - \text{ratio}) + Ar$$

where h(k) is the histogram (normalized) of the image; sh(k) is the spatial correlated histogram of the image; and 0≤ratio≤1.

If the number of values exceeds Pb, the number of pixel values exceeds an expected range, possibly indicating that pixels in this region have diagnostic relevance. In such a case, a combination step 735 is executed for histogram equalization (HE), using spatial correlation histogram equalization (SCHE), a method described in more detail in commonly assigned U.S. patent application Ser. No. 11/549,130 entitled "Method For Enhanced Visualization Of Medical Images" filed Oct. 13, 2006, incorporated herein by reference.

Figure 12:
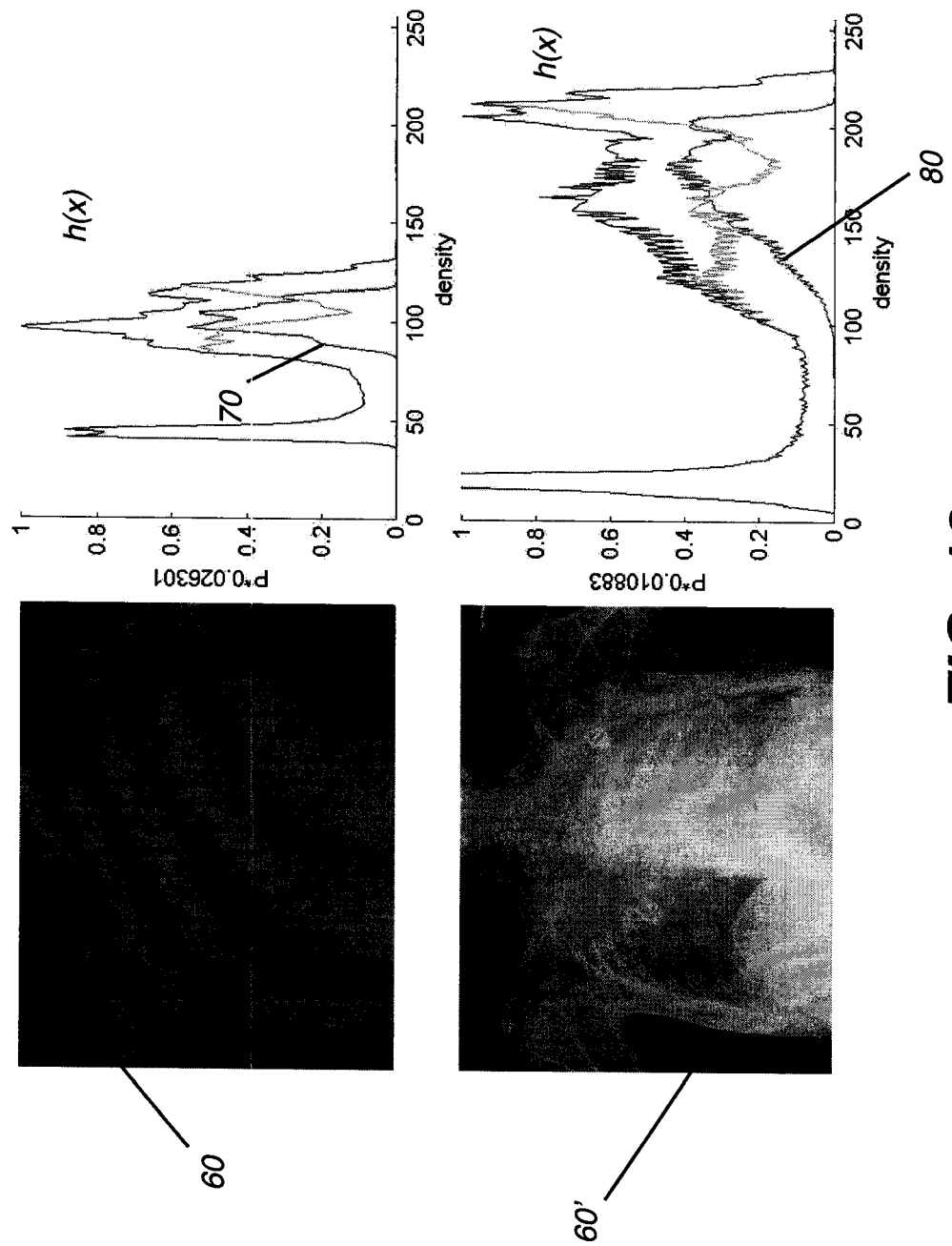
FIG. 12 shows and example of the effects of remapping image data for an image having significant image content.

FIG. 12 shows an example of a chest x-ray image 60 that shows improvement following the image transformation of the present invention. A transformed image is denoted as image 60'. Histograms to the right of images 60 and 60' show the effect of transformation and re-mapping on primary area 70 for this image.

In an LUT generation step 160 in FIG. 2, suitable look-up tables (LUTs) are provided for processing each of the images prior to submission to CAD processing.

Figure 13:
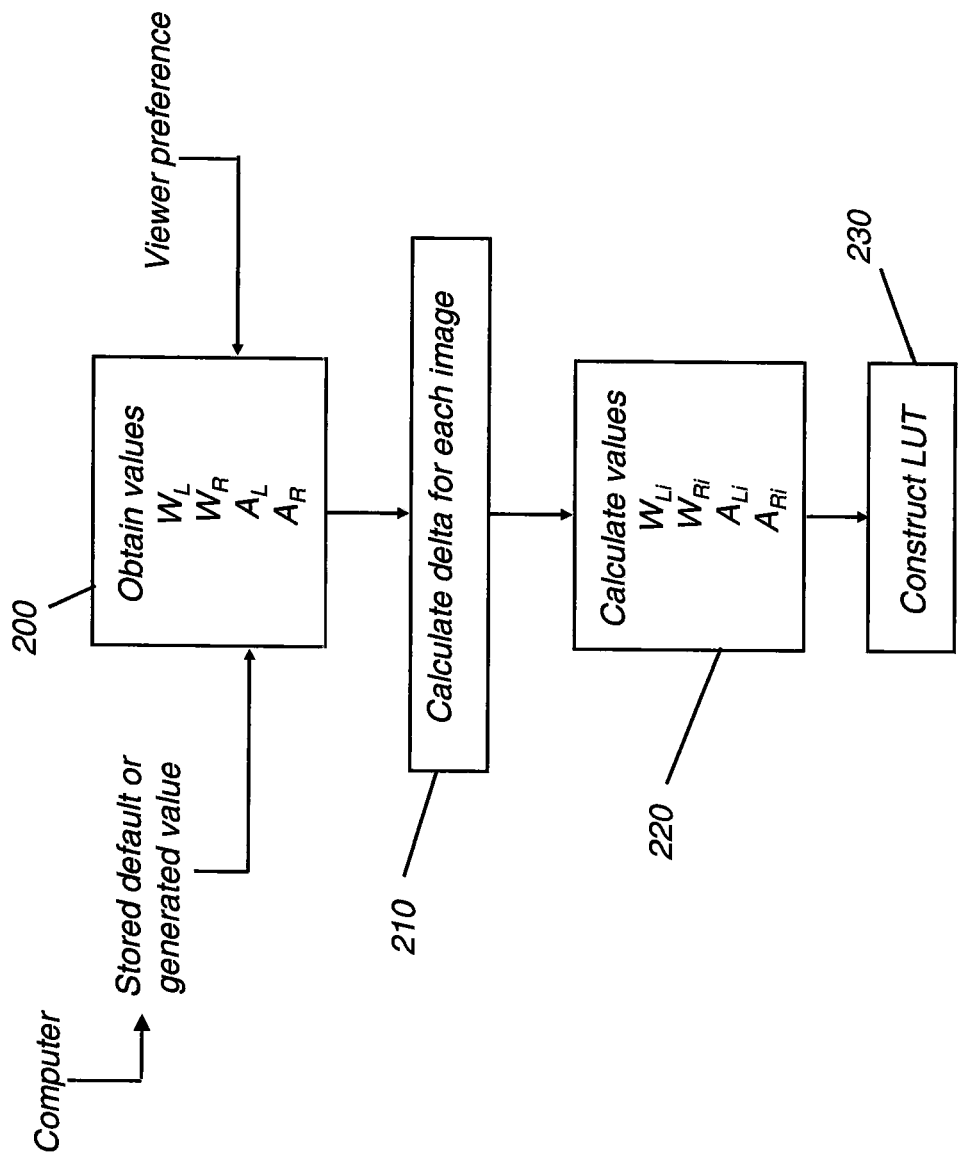
FIG. 13 is a flow chart showing steps for LUT generation in one embodiment.

The logic flow diagram of FIG. 13 shows how consistency processing provides localized control of image rendering in one embodiment. In an obtain values step 200, target values $W_L, W_R, A_L$, and $A_R$ are obtained as control points. These can be from values stored in memory and assigned for use with particular images. Alternately, these target values can be obtained from viewer preference data, using values entered directly by the viewer or using derived values from viewer selections. For example, these can be averaged values obtained from taking the results of testing for a number of practitioners. Next, in a calculate deltas step 210, delta or difference values are calculated for the image, or for the area of interest identified within the image. These values can be variable within a range set by the viewer or by the software application, so that the delta $\Delta$ values that yield $W_L \pm \Delta$ and $W_R \pm \Delta$ do not vary by more than a limited amount. For value $W_L$, for example, it can be specified that the acceptable range lies between $W_{Lmin}$ and $W_{Lmax}$, so that:

$W_{Lmin} < W_L < W_{Lmax}$

The value of delta for any image can be fixed or may be based on analysis of the individual image or on other factors related to the system, technique used, or patient, as described earlier. This value can be zero or other suitable value for any image.

Still referring to FIG. 13, a calculate mapping values step 220 calculates the corresponding values for the image, taking the delta value within account, that is, values: $W_{Li}, W_{Ri}, A_{Li}$, and $A_{Ri}$, where i indicates the image. This calculation then provides points that define a linear or other portion of a tone curve, as shown in the example of FIG. 5. An LUT generation step 230 uses this tone curve relationship in order to generate the LUT used for mapping input code values in the image to output code values for consistent rendering.

Using the method of the present invention, one or more images taken from the same patient, at any of a number of different equipment settings, can be provided with consistent treatment, so that evaluation of a single image or comparison of two or more images, either visually or using CAD assessment utilities, can be facilitated. The methods and apparatus of the present invention can help to provide improved care in an ICU or other type of critical care facility. Particularly well suited to support longitudinal tracking, the methods of the present invention can be used to provide imaging and other data in a chronologically sequenced arrangement, helping the clinician to be alerted to changes in the condition of a patient that can be detected using image and measured data. The present invention helps to standardize the presentation of image data so that information can be provided to medical personnel in a form that is straightforward to understand and to use. As was noted earlier, the method of the present invention provides pre-processing for one or more images, enabling a more accurate comparison between images that may have been taken at different times, by different operators, or under different imaging conditions. In one embodiment of the present invention, an image processing system performs the consistent rendering processes described earlier, then provides further enhancement for one or both of the consistently rendered images. Image enhancement methods could include, for example, those described in the '691 Barski reference, cited earlier.

In embodiments of the present invention, consistent rendering is a networked function, able to handle the diagnostic image data at any of several points in the imaging process. Consistent rendering modules can be programmed to handle raw data or rendered data, including image data stored in an image archival system.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, as noted earlier, any of a number of different methods could be used for background segmentation step 106. The apparatus and methods of the present invention can be employed for diagnostic images obtained from any of number of different types of diagnostic imaging systems, including x-ray, mammography, computed tomography, and MRI imaging systems, for example.

Thus, what is provided is an apparatus and method for enhancing a diagnostic image in order to provide consistent rendering for images obtained from one or more imaging systems connected to a network.

PARTS LIST

20. Image capture device
22. Image data
24. Image processing system
28. Archival system
30. Display
34, 36 Consistent rendering processor
40. Network
42. Imaging system
44. Imaging site
50. Consistency control module
52. Logic circuitry
54. Memory
56. Instructions
58. Network interface
60, 60'. Image
62. Mask
70, 70a, 70b. Primary area
80, 80a, 80b. Adjusted primary area
84, 88. Histogram
90. ROI region
92. Shoulder region
94. Toe region
100. Initial step
106. Type identification step
110. Landmark identification step
120. Control point identification step
130. Mapping step
160. LUT generation step
200. Obtain values step
210. Calculate deltas step
220. Calculate mapping values step
230. LUT generation step
400. Input step
410. ROI identification step
420. Range identification step
430. Matching step
440. Modification step
450. LUT generation step
700. Gray level partitioning step
710. ROI region LUT construction step
711. Obtain values step
712. Image size reduction step
713. Image activity determination step
714. LUT generation step
720. Toe region LUT construction step
721. Partial LUT construction step
722. Calculate pixel number step
723. Pixel number check step
724. Pixel value change step
725. Low value LUT step
726. Toe LUT construction step 730. Shoulder region LUT construction step
731. Set Wr value step
732. Partial LUT construction step
733. Calculate pixel number step
734. Pixel number check step
735. Combination step
736. Shoulder LUT construction step
dh(x). Difference histogram
h(x). Histogram
elp. Effective left point
erp. Effective right point
lp. Left point
rp. Right point
Al, $A_L$, $A_{Li}$. Remapped left point
Ar, $A_R$, $A_{Ri}$. Remapped right point
CP1, CP1', CP2. Control point
$L_c$. Column length
Wl, $W_L$, $W_{Li}$. Lower left point
Wr, $W_R$, $W_{Ri}$. Upper right point

The invention claimed is:

1. A method for rendering a diagnostic image executed at least in part by a computer, comprising:
   obtaining image data as input code values for the diagnostic image;
   processing the image data electronically to identify at least one anatomical feature and at least one anatomical region of interest within the image content for the diagnostic image;
   adjusting the image data depending on an identified type of the at least one anatomical feature;
   identifying one or more control points from within the at least one anatomical region of interest, wherein the one or more control points are calculated from histogram data;
   mapping the input code value of each of the one or more control points to a corresponding predetermined code value; and
   forming a look-up table that maps the input code value for each pixel value to a remapped value in the range defined by the output value of the control points.

2. The method of claim 1 further comprising adjusting the predetermined code values using stored difference values provided for a particular diagnostic imaging apparatus.

3. The method of claim 1 further comprising adjusting the predetermined code values using stored difference values computed according to statistical values obtained from the diagnostic image data.

4. A method for rendering a diagnostic image executed at least in part by a computer, comprising:
   obtaining image data as input code values for a diagnostic image;
   identifying one or more anatomical features and one or more anatomical regions of interest;
   adjusting the image data depending on the identified one or more anatomical features;
   identifying one or more of the input code values as control points from the one or more anatomical regions of interest, wherein the one or more control points are calculated from histogram data;
   mapping the input code value of each of the one or more control points to a corresponding predetermined output code value; and
   forming a look-up table that maps each of the rest of the input code values in the diagnostic image to a remapped value according to the mapping of the one or more control points.

5. The method of claim 4 wherein identifying one or more input code values as control points comprises:
   identifying the input code values of one or more points in the one or more anatomical regions of interest.

6. A method for rendering a diagnostic image, executed at least in part by a computer, the method comprising:
   obtaining image data as input code values for the diagnostic image;
   processing the image data electronically to identify at least one anatomical feature and at least one anatomical region of interest within the image content for the diagnostic image;
   adjusting the image data depending on an identified type of the at least one anatomical feature; and
   remapping the input code values for the at least one anatomical region of interest to output code values for the diagnostic image and generating a look-up table with the steps of:
   (i) identifying at least one control point from the at least one anatomical region of interest in the input code values;
   (ii) mapping the at least one control point to an output code value; and
   (iii) mapping other input code values to output code values according to the mapping of the at least one control point and forming the look-up table according to the mapping,
   wherein the at least one control point is calculated from histogram data.

7. The method of claim 6 wherein mapping the at least one control point to the output code value further comprises adjusting the output code value according to at least one of the type of image, the imaging system used, exposure settings used, a template image, and patient positioning.

8. The method of claim 6 wherein obtaining image data comprises obtaining rendered image data.

9. The method of claim 6 wherein obtaining image data comprises obtaining the data directly from an image capture apparatus.

10. The method of claim 6 wherein identifying at least one control point comprises identifying a boundary point for a range of output code values.

11. A networked system for rendering diagnostic image data for display, comprising:
   at least one diagnostic imaging apparatus that obtains digital image data for a patient and that is in communication with a computer network;
   at least one consistency control module that executes at a networked processor on the computer network and that is operatively responsive to a set of programmed instructions that comprise:
   (a) instructions for accessing the obtained digital image data and for detecting a type of image for the digital image data obtained from the networked diagnostic imaging apparatus;
   (b) instructions for identifying one or more anatomical features, one or more anatomical regions of interest, and one or more control points from the one or more anatomical regions of interest in the obtained digital image data, wherein the one or more control points are calculated from histogram data;
   (c) adjusting the obtained digital image data depending on a type of the one or more anatomical features identified;
   (d) instructions for mapping input code values of the one or more control points to corresponding predetermined code values;

(e) instructions for mapping additional input code values to output values according to the mapping of the one or more control points; and (f) instructions for providing rendered image data as output according to the mapped output values; and a DICOM destination in networked communication with the at least one consistency control module for storing or displaying the rendered.

12. The networked system of claim 1 wherein the at least one diagnostic imaging apparatus is a digital radiographic system.

13. The networked system of claim 1 wherein the digital image data is from a previously rendered image.

14. The networked system of claim 1 wherein the programmed instructions for the mapping of input code values form a look-up table.

15. The networked system of claim 1 wherein the DICOM destination is a display monitor.

16. The networked system of claim 1 wherein the programmed instructions further comprise instructions for identifying a region of interest.

17. The networked system of claim 1 wherein the at least one consistency control module is associated with a specific radiography imaging system.

18. The networked system of claim 1 wherein the instructions for adjusting the mapping are generated according to one or more of an electronically stored template image, a stored variable, results of image analysis, and viewer preference data.

19. The networked system of claim 1 wherein the DICOM destination is an archival system.

\* \* \* \* \*

UNITED STATES PATENT AND TRADEMARK OFFICE
CERTIFICATE OF CORRECTION

PATENT NO. : 8,588,485 B2  Page 1 of 1
APPLICATION NO. : 12/482651
DATED : November 19, 2013
INVENTOR(S) : Zhimin Huo et al.

It is certified that error appears in the above-identified patent and that said Letters Patent is hereby corrected as shown below:

In the Specification

Column 10, line 24    Please replace: "$(Al + \Delta l, Ar + Ar)$" with
--$(Al + \Delta l, Ar + \Delta r)$--

Signed and Sealed this
Twenty-third Day of September, 2014

Michelle K. Lee
*Deputy Director of the United States Patent and Trademark Office*